(12) United States Patent
Miller et al.

(10) Patent No.: US 7,700,790 B2
(45) Date of Patent: Apr. 20, 2010

(54) ALKYLENE OXIDE PROCESS

(75) Inventors: Jay F. Miller, Chester Springs, PA (US); Te Chang, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 286 days.

(21) Appl. No.: 11/588,453

(22) Filed: Oct. 27, 2006

(65) Prior Publication Data

US 2008/0103319 A1 May 1, 2008

(51) Int. Cl.
*C07D 301/12* (2006.01)
*C07D 301/06* (2006.01)

(52) U.S. Cl. .................. 549/532; 549/531; 549/533

(58) Field of Classification Search ............. 549/531, 549/532, 533
See application file for complete search history.

(56) References Cited

U.S. PATENT DOCUMENTS

| 6,005,123 A | 12/1999 | Dessau et al. | 549/531 |
|---|---|---|---|
| 6,008,388 A | 12/1999 | Dessau et al. | 549/531 |
| 6,498,259 B1 | 12/2002 | Grey et al. | 549/533 |

FOREIGN PATENT DOCUMENTS

| JP | 4-352771 | 12/1992 |
|---|---|---|
| JP | H8-269029 | 10/1996 |
| JP | H8-269030 | 10/1996 |

OTHER PUBLICATIONS

Kirk-Othmer, *Encyclopedia of Chemical Technology*, 4th Edition, vol. 9, (1994), pp. 163-164 and 343-345.

*Primary Examiner*—Bernard Dentz
(74) *Attorney, Agent, or Firm*—Kevin M. Carroll

(57) ABSTRACT

A process is provided for the production of alkylene oxide by catalytic reaction of olefin, hydrogen and oxygen in the presence of promoting buffer salts, the improvement wherein the buffer salts are recovered by electrodialysis and/or crystallization and recycled to the catalytic reaction.

6 Claims, 2 Drawing Sheets

ALKYLENE OXIDE PROCESS

FIELD OF THE INVENTION

The present invention relates to the preparation of alkylene oxides such as propylene oxide by the catalytic reaction of olefin, oxygen and hydrogen. The reaction is carried out in the presence of various salts which improve the activity and selectivity of the process. The present invention is concerned with the recovery and recycle of such salts.

BACKGROUND OF THE INVENTION

Alkylene oxides such as propylene oxide are important materials of commerce. Processes for the preparation of the alkylene oxides include the chlorohydrin process as well as the hydroperoxide route; see, for example, U.S. Pat. No. 3,351,635. Because the chlorohydrin process is costly and produces polluting byproducts and the hydroperoxide process produces a coproduct such as styrene or TBA, the industry has sought an improved direct oxidation process for alkylene oxide production.

One such improved process is the production of propylene oxide by reaction of propylene, oxygen and hydrogen in the presence of an appropriate catalyst or mixture of catalysts. See for example, Japanese Kokai No. 4-352771, JP H8-269029, JP H8-269030, U.S. Pat. No. 6,005,123, U.S. Pat. No. 6,005,123, U.S. Pat. No. 6,498,259 and the like, the disclosures of which are incorporated herein by reference. A useful description of the production of propylene oxide by reaction of propylene, oxygen and hydrogen in a salt buffered system is found in U.S. Pat. No. 6,498,259.

In such systems, the recovery and recycle of buffer salts is of considerable importance insofar as the overall economics of the process is concerned.

SUMMARY OF THE INVENTION

The present invention provides a process whereby buffer salts such as described in U.S. Pat. No. 6,498,259 are separated from a reaction mixture resulting from the epoxidation reaction of olefin, hydrogen and oxygen to form alkylene oxide; the separation is accomplished by crystallization as shown in FIG. 2 and/or by electrodialysis as shown in FIG. 1 with the separated salts being recycled to the epoxidation reaction.

DESCRIPTION OF THE DRAWING

The accompanying drawings illustrate schematically various practices of the invention.

DETAILED DESCRIPTION

Figure 1:
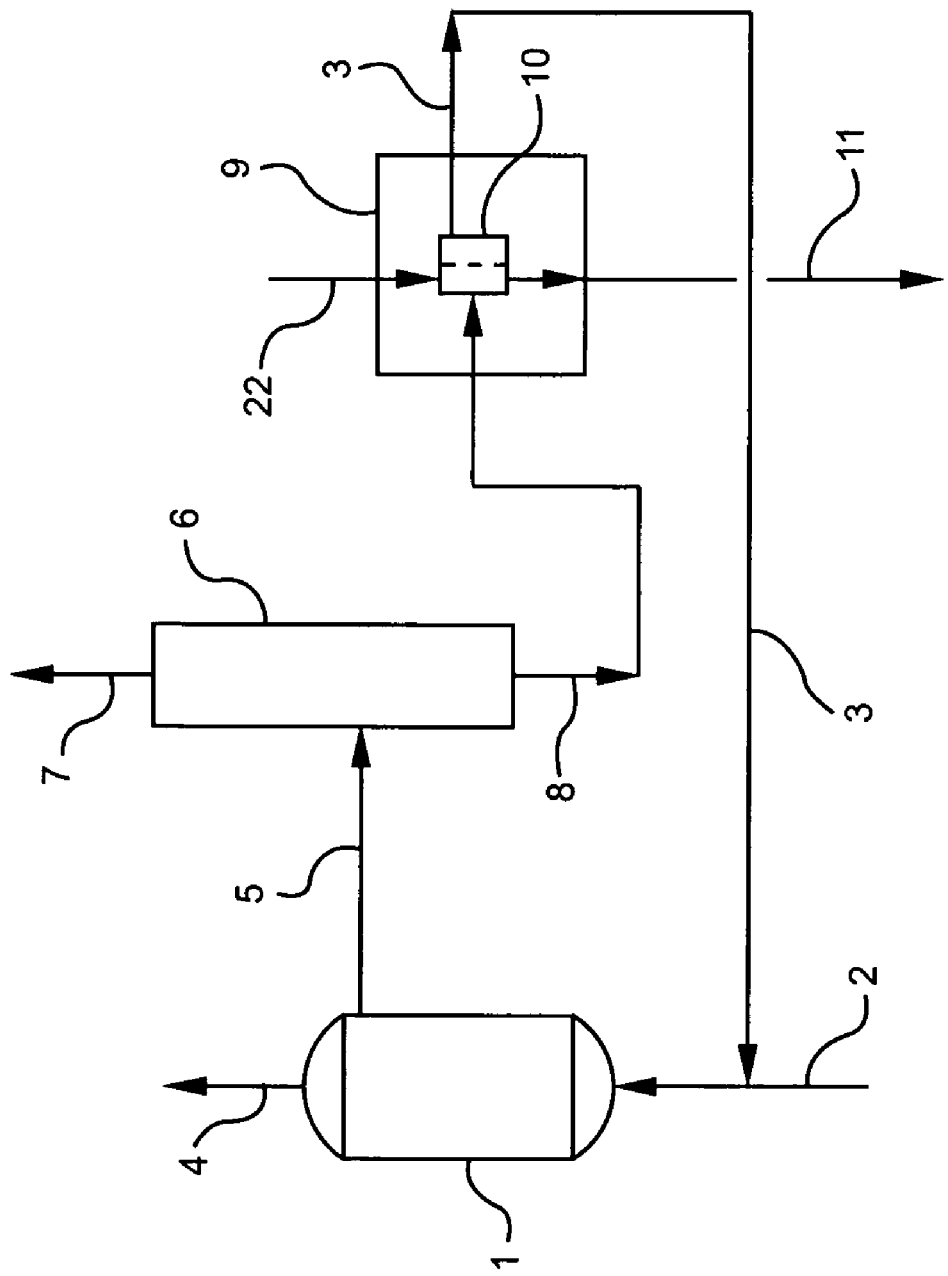
FIG. 1 illustrates schematically practice of the invention wherein electrodialysis is used to separate buffer salts.

Attached FIG. 1 illustrates practice of the invention wherein the buffer salts are separated by electrodialysis and recycled to the epoxidation reactor.

Referring to FIG. 1, reactor 1 is a conventional epoxidation reactor which may be a slurry or fixed bed catalytic reactor. A suitable epoxidation catalyst such as a palladium promoted TS-1 catalyst is provided to catalyze production of the epoxide product in accordance with known procedures.

A feed mixture comprised of olefin, oxygen, hydrogen and diluent is introduced to reactor 1 via line 2 along with appropriate solvent such as methanol or a methanol-water mixture.

As described in U.S. Pat. No. 6,498,259, the reaction is carried out in the presence of a buffer salt which preferably is a salt of an oxy acid. Alkali metal and ammonium phosphate are especially preferred. An aqueous solution of buffer salt is introduced via line 3 sufficient to provide a reaction mixture pH in reactor 1 of 3 to 10, preferably 4 to 9 and most preferably 4.5 to 7.5.

The reaction is carried out in reactor 1 in accordance with known procedures to produce alkylene oxide, most preferably propylene oxide. Vapor components such as oxygen and hydrogen are removed from reactor 1 via line 4 and a liquid reaction mixture comprised of alkylene oxide product, various byproducts, solvent and buffer salts is removed via line 5.

The liquid mixture passes via line 5 to distillation zone 6 where alkylene oxide product along with other materials is distilled overhead via line 7 from an aqueous solution of buffer salts which is removed as bottoms via line 8.

From zone 6, the aqueous mixture comprising buffer salts is passed via line 8 to electrodialysis zone 9 for concentration of the buffer salts for recycle to reactor 1.

Electrodialysis is, by now, a well known technology whereby ions are moved across ion exchange membranes under the influence of a direct electric current. See Kirk-Othmer "Encyclopedia of Chemical Technology, 4th Edition, pages 163-164 and 343-345, Vol. 9 (1994). In accordance with this invention, electrodialysis cell 9 is provided effective to pass buffer salts through appropriate membranes while essentially preventing passage of other materials there through.

Electrodialysis cell 9 comprises a plurality of ion-selective membrane containing electrolytic cells 10 adapted to separate buffer salts from the other reaction mixture components. The cells are multicompartmented cells in which membranes selective to anions are alternated with membranes selective to cations. Two liquid streams are fed to the electrodialysis unit: stream 8 distillation bottoms from column 6 which contains buffer salts and stream 22 which is a water or water/methanol stream. For example, every even numbered compartment will have either a water or water/methanol stream entering. The odd numbered compartments have the effluent from distillation column 8. A d-c potential is applied whereby cations tend to move toward the negatively charged cathodes and anions tend to move toward the positively charged anode. A general description of such cells is found at P. 343 of Kirk-Othmer, Vol. 9. The odd number compartments, containing the reaction mixture from distillation column 8, becomes depleted in buffer salts and the resulting reaction mixture reduced in salts is removed via line 11 for further processing, and preferably is recycled back to stream 2. Aqueous solution of aqueous/methanol solution containing the separated buffer salts is removed via line 3 and recycled to reactor 1.

Frequently it is advantageous to adjust the pH of this recycle stream (not shown) to achieve optimum results in the epoxidation reaction.

The desalted solution is removed from electrodialysis unit 9 via line 11, this solution can be recycled to line 2 and thence to reactor 1 or passed to waste disposal or to distillation to recover water and organics (not shown).

Figure 2:
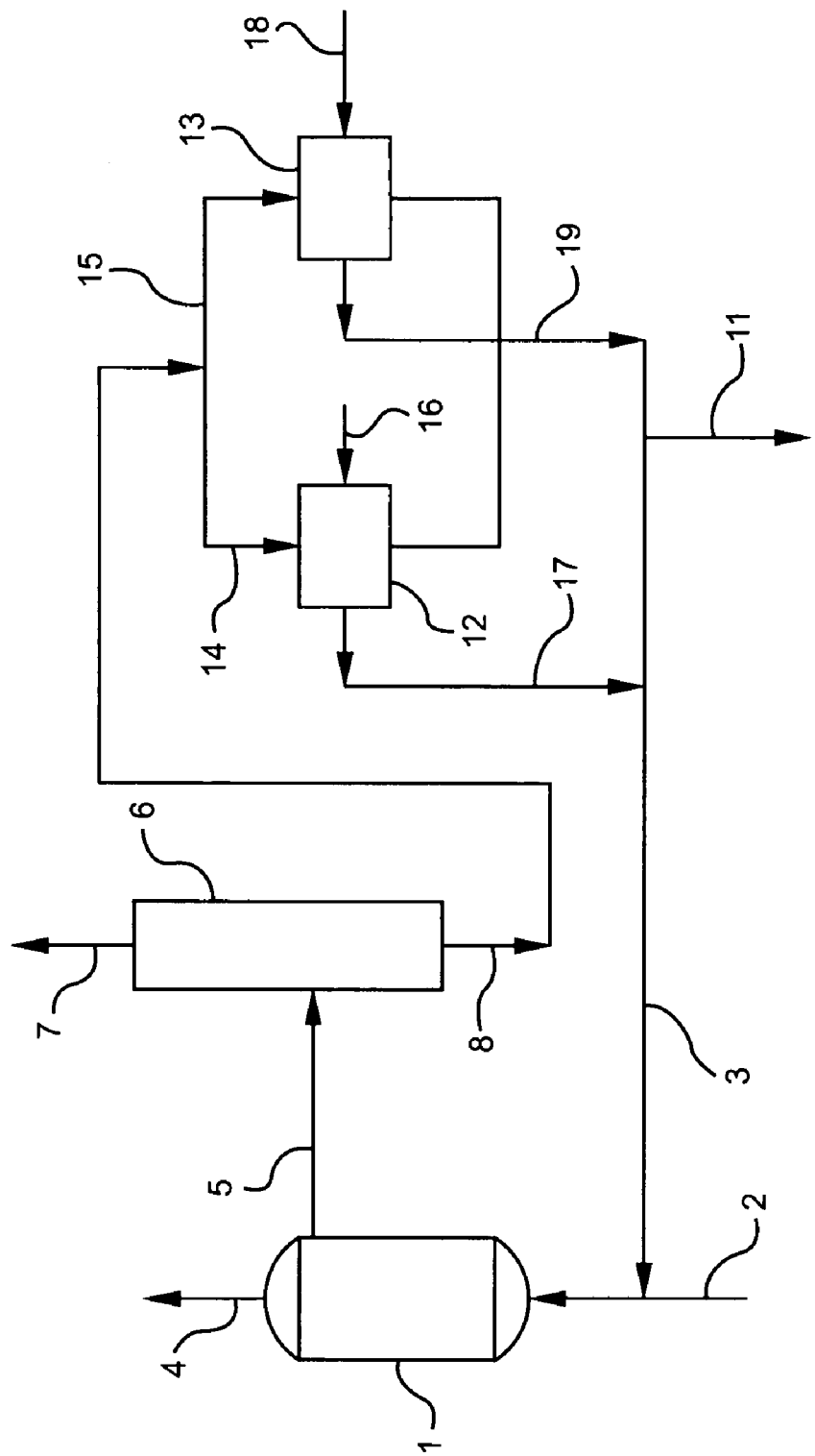
FIG. 2 illustrates schematically practice of the invention wherein falling film crystallization is used to separate buffer salts.

An alternative practice of the invention which involves crystallization in place of electrodialysis is illustrated in FIG. 2.

Referring to FIG. 2, reactor 1 is operated as described in connection with FIG. 1. In distillation zone 6 light materials, product alkylene oxide and optionally solvent are separated overhead from aqueous buffer salt bottoms.

Falling film crystallizers 12 and 13 are provided with appropriate piping means such that the crystallizers operate alternatively. For example, the buffer salt solution can first be passed to crystallizer 12 by means of line 14 and subjected to falling film crystallization therein. When the buffer salt crystals have accumulated on the crystallizer surfaces to the desired extent, the buffer salt solution is directed via line 15 to falling film crystallizer 13 wherein similar crystallization takes place. While crystallization is talking place in crystallizer 13, water is introduced to crystallizer 12 via line 16 to dissolve the crystallized salts and the salt containing solution passes via lines 17 and 3 back to reactor 1.

When salts have accumulated to the desired extent in crystallizer 13, the solution from zone 6 is directed back to crystallizer 12 and the crystals in crystallizer are dissolved in water introduced via line 18 and the aqueous salt solution passed via lines 19 and 3 back to reactor 1. By alternating the crystallizers, continuous operation can be achieved.

The falling film crystallizers 12 and 13 are known apparatus. Generally, a plurality of tubes are provided which are externally cooled and through which the buffer salt containing stream from column 6 passes. Salts are crystallized from the stream and deposit on the inner surfaces of the crystallization tubes. When a desired amount of crystallized salts have been deposited, for example, in crystallizer 12, the salt containing stream is directed to the alternate crystallizer 13 for continued crystallization while the crystallized salts in crystallizer 12 are redissolved, as in heated water.

The dissolved buffer salt solutions may have various materials added thereto (not shown) to provide the necessary pH values in reactor 1.

In another embodiment, in place of a plurality of falling film crystallizers, conventional crystallizers can be provided whereby buffer salt crystals are recovered by filtration and/or centrifugation, redissolved in water and recycled to reactor 1.

EXAMPLE 1

Propylene, hydrogen and oxygen are reacted in reactor 1 according to conventional procedures to form propylene oxide. A methanol and water solvent mixture is employed in which a 2 wt. % Pd on TS-1 catalyst is slurried. The reaction mixture is maintained at a Ph of 5.0 by addition of an aqueous solution of sodium phosphate, alternatively ammonium phosphate can be used.

The reaction mixture is distilled in column 6 and a bottoms stream comprised by weight of 20% water, 78.9% methanol, 0.1% sodium phosphate, and 1% others is passed via line 8 to electrodialysis zone 9.

In zone 9 there is provided a plurality of ion-selective membrane-containing electrolytic cells with alternating membranes selective to anions such as NEOSEPTA AMX made by Tokayama Soda, and membranes selective to cations such as NEOSEPTA CMX also made by Tokayama Soda. A d-c potential is applied whereby cations tend to move toward the negatively charged cathode and anions tend to move toward the positively charged anode. The permeated sodium and phosphate ions are recombined in aqueous solution and passed via line 3 back to reactor 1. The solution depleted in sodium phosphate is separated via line 11 and may be discarded or further treated.

The recovery of sodium phosphate is about 99%.

EXAMPLE 2

Propylene, hydrogen and oxygen are reacted in reactor 1 according to conventional procedures to form propylene oxide. A methanol and water solvent mixture is employed in which a 2 wt. % Pd on TS-1 catalysts is slurried. The reaction mixture is maintained at a Ph of 5.0 by addition of an aqueous solution of sodium phosphate.

The reaction mixture is distilled in column 6 and a bottoms stream comprised by weight of 20% water, 78.9% methanol, 0.1% sodium phosphate, and 1% others is passed via line 8 to falling film crystallizers 12 and 13 for buffer separation. As described above, the crystallizers are operated alternately such that while one is crystallizing the buffer salt the other is regenerating. Illustratively, the bottoms stream first passes via line 14 to falling film crystallizer 12 wherein the sodium phosphate crystallizers at 0° C. on the crystallizer surfaces. After about 120 minutes, the bottoms stream is redirected via line 15 to crystallizer 13 where comparable crystallization takes place. While crystallization is taking place in crystallizer 13, hot water is introduced to crystallizer 12 via line 16 in order to redissolve the sodium phosphate buffer. Similarly, when crystallizer 12 is in crystallization mode, hot water is introduced via line 18 to redissolve sodium phosphate, the solution being removed via line 19. The redissolved buffer salt solutions are returned to reactor 1 via line 17 and 19 and line 3.

The solution depleted in sodium phosphate is separated via line 11 and may be discarded.

The recovery of sodium phosphate is about 90%.

We claim:

1. In a process for the production of alkylene oxide by catalytic reaction of olefin, oxygen and hydrogen in a solvent comprised of methanol or a mixture of methanol and water wherein the reaction is modified by the presence of buffer salts in the reaction mixture, the improvement which comprises recovering the buffer salts by electrodialysis and/or crystallization and recycling the recovered buffer salts to the catalytic reaction.

2. The process of claim 1 wherein the alkylene oxide is propylene oxide.

3. The process of claim 1 wherein the reaction mixture pH is maintained at a value of 3-10.

4. The process of claim 1 wherein the buffer salts are recovered by electrodialysis.

5. The process of claim 1 wherein the buffer salts are recovered by crystallization.

6. The process of claim 1 wherein the buffer salts are alkali metal or ammonium phosphates.

* * * * *